United States Patent
Matsubara et al.

(10) Patent No.: US 9,417,222 B2
(45) Date of Patent: *Aug. 16, 2016

(54) GAS ANALYZER

(71) Applicant: NIHON KOHDEN CORPORATION, Tokyo (JP)

(72) Inventors: Isao Matsubara, Tokyo (JP); Yutaka Uchiyama, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 191 days.

This patent is subject to a terminal disclaimer.

(21) Appl. No.: 14/273,529

(22) Filed: May 8, 2014

(65) Prior Publication Data

US 2014/0247130 A1    Sep. 4, 2014

Related U.S. Application Data

(63) Continuation of application No. 13/015,163, filed on Jan. 27, 2011, now Pat. No. 8,823,533.

(30) Foreign Application Priority Data

Jan. 28, 2010    (JP) ................. 2010-017406

(51) Int. Cl.
*G08B 17/10* (2006.01)
*G08B 1/08* (2006.01)
*G01N 33/00* (2006.01)
(Continued)

(52) U.S. Cl.
CPC ............ *G01N 33/0004* (2013.01); *A61B 5/097* (2013.01); *G01N 33/0014* (2013.01); *G08B 21/18* (2013.01); *A61B 5/082* (2013.01);
(Continued)

(58) Field of Classification Search
CPC ............... G08B 17/11; G08B 21/0211; G08B 21/0423; G08B 21/0453; G08B 21/0461; G08B 21/0469; G01N 21/783; G01N 27/4045; G01N 33/004; G06F 19/3418; Y02B 30/78; Y02B 90/242; Y02B 90/244
See application file for complete search history.

(56) References Cited

U.S. PATENT DOCUMENTS 4,274,425 A    6/1981 Lutz et al.
4,713,095 A    12/1987 Ricciardelli
(Continued)

FOREIGN PATENT DOCUMENTS

CN    2754699 Y    2/2006
EP    0 707 827 A1    4/1996
(Continued)

OTHER PUBLICATIONS

Photos 1-7 show a gas analyzer. One of the photos shows the serial number of the gas analyzer indicating that it was made in the year 2007. The photos also show that the gas analyzer device has a holder portion that can be rotated 90 degrees.
(Continued)

*Primary Examiner* — Emily C Terrell
(74) *Attorney, Agent, or Firm* — Pearne & Gordon LLP

(57) ABSTRACT

A gas analyzer includes: a gas measuring portion which performs a measurement on a gas; a case which houses the gas measuring portion; a liquid separator which includes a reservoir for storing a liquid component separated from the gas; a holder portion which holds the liquid separator; and a rotation mechanism which mounts the holder portion to the case.

11 Claims, 19 Drawing Sheets

(51) Int. Cl.
*A61B 5/097* (2006.01)
*G08B 21/18* (2006.01)
*A61B 5/08* (2006.01)
*A61B 5/083* (2006.01)
*A61B 5/091* (2006.01)
*G01N 33/497* (2006.01)

(52) U.S. Cl.
CPC ............... *A61B5/083* (2013.01); *A61B 5/091* (2013.01); *G01N 33/497* (2013.01)

(56) References Cited

U.S. PATENT DOCUMENTS

| | | | |
|---|---|---|---|
| 4,924,860 A | 5/1990 | Larsen et al. | |
| 4,997,463 A | 3/1991 | Ricciardelli | |
| 5,231,991 A | 8/1993 | Nelson | |
| 5,291,898 A * | 3/1994 | Wolf | 600/532 |
| 5,379,749 A | 1/1995 | Rieke et al. | |
| 5,452,714 A | 9/1995 | Anderson et al. | |
| 5,616,158 A | 4/1997 | Biendarra et al. | |
| 5,749,355 A | 5/1998 | Roan et al. | |
| 5,797,426 A | 8/1998 | Powell | |
| 5,826,577 A | 10/1998 | Perroz, Jr. et al. | |
| 6,471,853 B1 | 10/2002 | Moscaritolo | |
| 6,855,249 B2 | 2/2005 | Moscaritolo | |
| 6,923,847 B2 | 8/2005 | Larsen et al. | |
| 7,364,553 B2 | 4/2008 | Paz et al. | |
| 7,600,439 B1 * | 10/2009 | Patterson et al. | 73/863.21 |
| 7,914,460 B2 * | 3/2011 | Melker et al. | 600/532 |
| 7,993,281 B2 * | 8/2011 | Stock | A61B 5/097 600/529 |
| 2004/0138577 A1 | 7/2004 | Kline | |
| 2004/0161804 A1 | 8/2004 | McCash et al. | |
| 2005/0263004 A1 | 12/2005 | Larsen et al. | |
| 2007/0173731 A1 | 7/2007 | Meka et al. | |
| 2009/0211448 A1 | 8/2009 | Mcclain | |
| 2014/0358020 A1 * | 12/2014 | Park | G01N 33/98 600/532 |

FOREIGN PATENT DOCUMENTS

| | | |
|---|---|---|
| JP | 62-154515 A | 7/1987 |
| JP | 63-185410 A | 8/1988 |
| JP | 1-305355 A | 12/1989 |
| JP | 7-120462 A | 5/1995 |
| JP | 2002-74921 A | 3/2002 |
| JP | 2003-14722 A | 1/2003 |
| JP | 2005-507073 A | 3/2005 |
| JP | 2009-75096 A | 4/2009 |

OTHER PUBLICATIONS

Product brochure showing a gas analyzer. 2007.
Japanese Office Action for the related Japanese Patent Application No. 2010-017406 dated Nov. 8, 2012.
Chinese Office Action for the related Chinese Patent Application No. 201110030377.8 dated Apr. 23, 2013.
Chinese Office Action for the related Chinese Patent Application No. 201110030377.8 dated Dec. 10, 2013.
European Office Action for the related European Patent Application No. 11 152 353.6 dated Feb. 17, 2014.

* cited by examiner

FIG. 18

| CONTACT IN SWITCH ON STATE | CASE ATTITUDE |
|---|---|
| SWa | a |
| SWb | b |
| SWc | c |
| SWd | d |

GAS ANALYZER

This application claims the priority benefit under 35 U.S.C. §120 and is a Continuation application of co-pending U.S. patent application Ser. No. 13/015,163 filed on Jan. 27, 2011, which is hereby incorporated in its entirety by reference. This application also claims the priority benefit under 35 U.S.C. §119 of Japanese Patent Application No. 2010-017406 filed on Jan. 28, 2010, which is hereby incorporated in its entirety by reference.

BACKGROUND OF THE INVENTION

The present invention relates to a sampling gas analyzer for analyzing a gas, or particularly effectively, a gas obtained from a living body.

A sampling respiratory gas analyzer is configured so that a gas to be measured is sucked into the interior of the analyzer, and then subjected to a measurement by a sensor in the analyzer. In such an analyzer, there is a fear of an adverse effect that water vapor contained in the gas to be measured condenses, and, when liquid is sucked into the interior of the analyzer, rust or the like occurs.

In order to solve the problem, a mechanism has been proposed in which liquid to be used in a respiratory gas analyzer is separated by separating the liquid by means of surface tension and capillary action, and then guiding the liquid to a cup (see U.S. Pat. No. 4,713,095). According to the apparatus, liquid which is formed by condensing water vapor contained in the gas to be measured can be separated. However, the apparatus has a problem in that, when the cup of the liquid separator does not exist in the direction of gravitational force of a condensing portion in order to receive the liquid produced by condensation, the liquid enters the interior of the apparatus.

In order to solve the problem, furthermore liquid separators incorporating a mechanism which uses a polymer absorbent, and which, when liquid enters the mechanism, performs a sealing function. Each of such separators is characterized in that the use of a polymer absorbent can prevent liquid from entering the interior of the separator (see U.S. Pat. Nos. 4,924, 860 and 6,923,847). However, each of the liquid separators remains to have a problem in that the function of separating liquid does not normally function unless the cup of the liquid separator exists in the direction of gravitational force of a condensing portion.

SUMMARY

It is therefore an object of the invention to provide a gas analyzer in which, both when the analyzer is placed in the usual state (for example, the horizontal state) and when the analyzer is placed in a state perpendicular to the usual state (for example, the vertical state), a liquid separator appropriately functions so that an adverse effect on the gas analysis can be prevented from occurring.

In order to achieve the object, according to the invention, there is provided a gas analyzer comprising: a gas measuring portion which performs a measurement on a gas; a case which houses the gas measuring portion; a liquid separator which includes a reservoir for storing a liquid component separated from the gas; a holder portion which holds the liquid separator; and a rotation mechanism which mounts the holder portion to the case.

The gas analyzer may further include: a locking unit which locks the holder portion in a case where the holder portion is rotated to a position where the reservoir is in a lowermost portion in a direction of gravitational force in the liquid separator.

The gas analyzer may further include: a sensor which detects an attitude of the holder portion with respect to a direction of gravitational force.

The gas analyzer may further include: an alarm unit which generates an alarm in a case where the attitude of the holder portion which is detected by the sensor is not in a predetermined attitude in which the reservoir is positioned in the lowermost portion in the direction of gravitational force in the liquid separator.

The gas analyzer may further include: a transmitting unit which transmits a detection signal in a case where the attitude of the holder portion which is detected by the sensor is not in a predetermined attitude in which the reservoir is positioned in the lowermost portion in the direction of gravitational force in the liquid separator.

In order to achieve the object, according to the invention, there is also provided a gas analyzer comprising: a gas measuring portion which performs a measurement on a gas; a case which houses the gas measuring portion; a holder portion that holds a liquid separator which includes a reservoir for storing a liquid component separated from the gas, and which guides the gas from which the liquid component is separated, to the gas measuring portion; and a holding unit which holds the liquid separator in one of attitudes which are different from one another in steps of 90 degrees.

The holding unit may include a main flow path through which the gas is flown from the liquid separator to the gas measuring portion, and sub flow paths for applying a sucking operation on the reservoir.

In a face of the holder portion which is opposed to the liquid separator, a flow path port of the main flow path, and sub flow path ports of the sub flow paths may be formed, the sub flow path ports being symmetrically placed about the flow path port of the main flow path.

The gas analyzer may further include: a sensor which detects an attitude of the liquid separator held by the holder portion with respect to a direction of gravitational force.

The gas analyzer may further include: an alarm unit which generates an alarm in a case where the attitude of the liquid separator detected by the sensor is not in a predetermined attitude in which the reservoir is positioned in the lowermost portion in the direction of gravitational force in the liquid separator.

The gas analyzer may further include: a transmitting unit which transmits a detection signal in a case where the attitude of the liquid separator which is detected by the sensor is not in a predetermined attitude in which the reservoir is positioned in the lowermost portion in the direction of gravitational force in the liquid separator.

BRIEF DESCRIPTION OF THE DRAWINGS

FIG. 18 is view showing correspondence relationships between the attitude of a case of the gas analyzer of the second embodiment of the invention, and switches constituting a second attitude sensor.

DETAILED DESCRIPTION OF EMBODIMENTS

Figure 1:
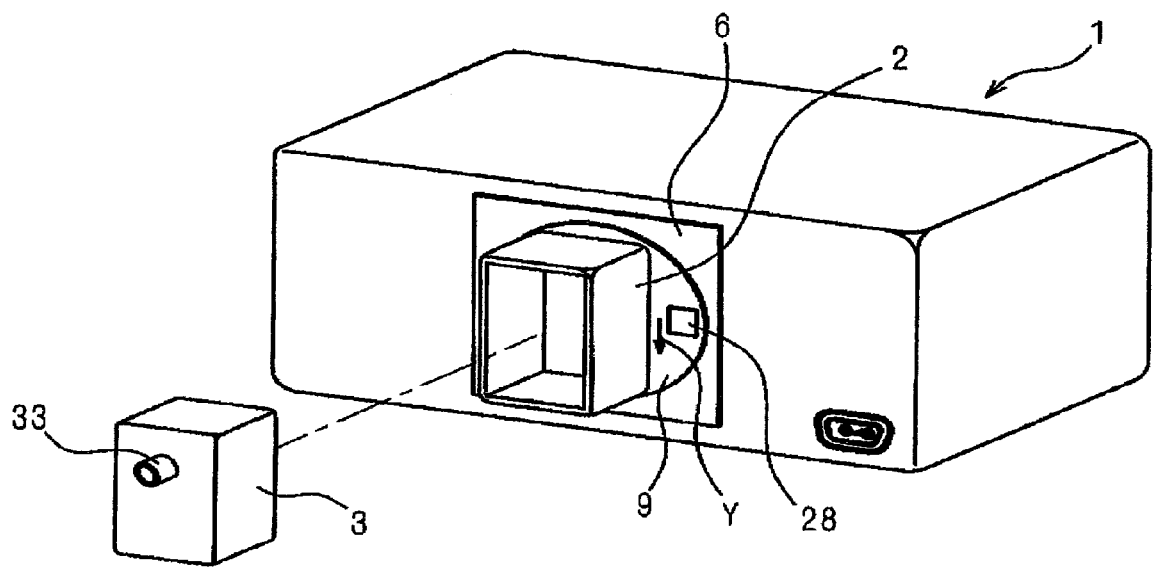
FIG. 1 is a perspective view showing a gas analyzer of a first embodiment of the invention.

Hereinafter, embodiments of the gas analyzer of the invention will be described with reference to the accompanying drawings. In the figures, the identical components are denoted by the same reference numerals, and duplicated description will be omitted. In a gas analyzer of a first embodiment, as shown in FIG. 1, fundamental functions are housed in a case 1, and a holder portion 2 having a bottomed rectangular cylindrical shape is projected from the sidewall of the outer front side.

Figure 2:
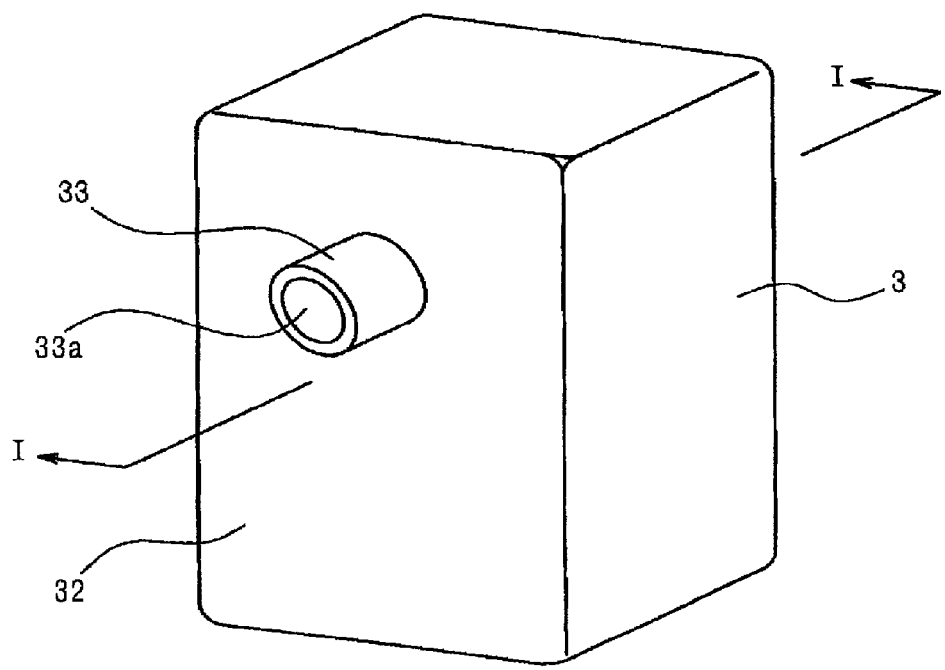
FIG. 2 is a perspective view showing a water trap which is applied to the gas analyzer of the first embodiment of the invention.
Figure 3:
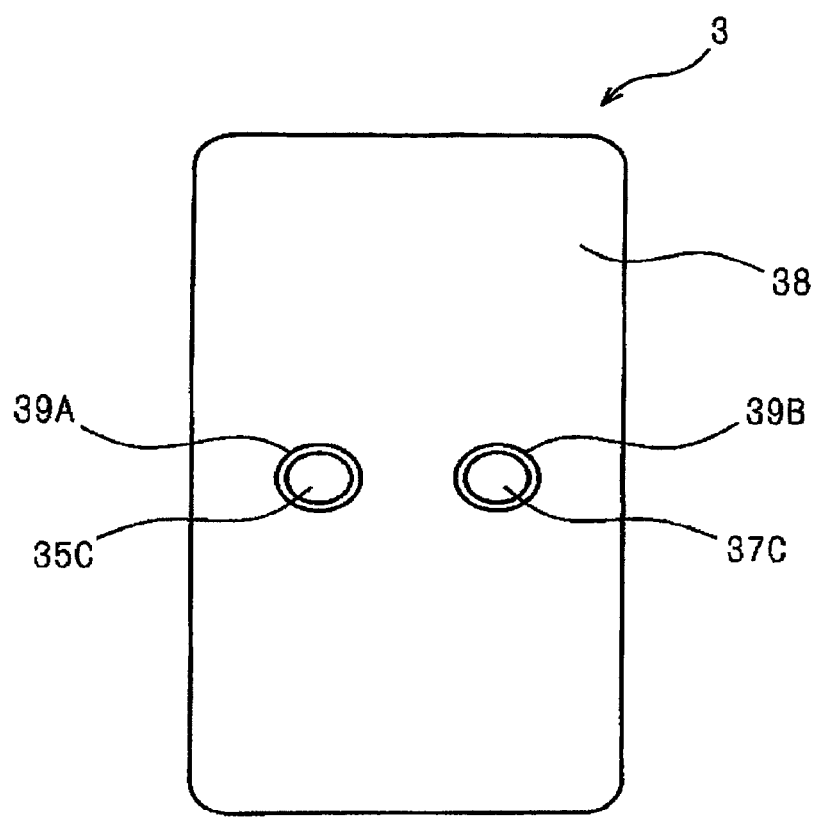
FIG. 3 is a rear view showing the water trap which is applied to the gas analyzer of the first embodiment of the invention.
Figure 4:
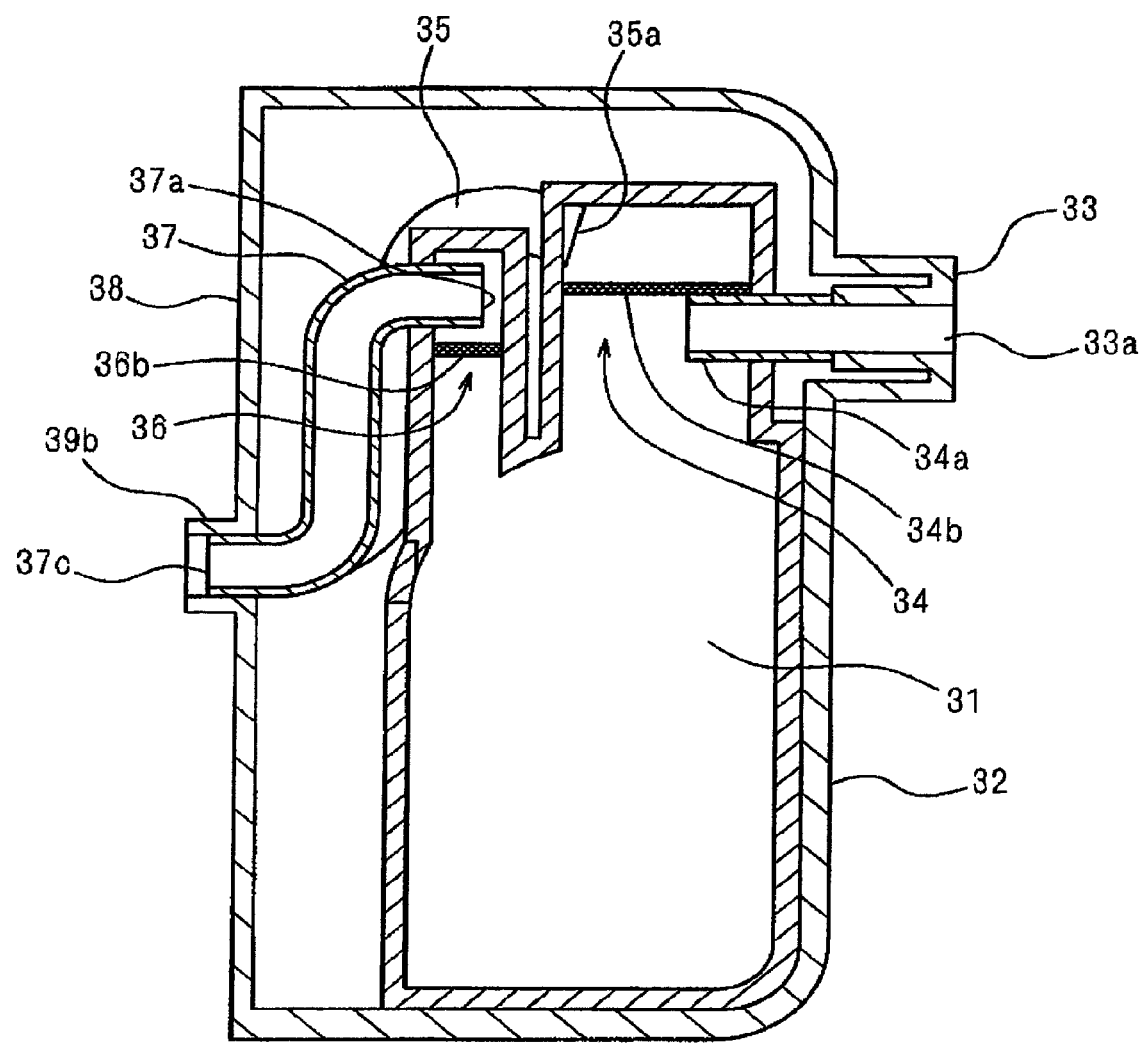
FIG. 4 is a sectional view taken along line I-I of FIG. 2.

A water trap 3 which is a liquid separator having a rectangular parallelepiped shape as shown in FIGS. 2 and 3 is inserted and fitted into the holder portion 2. As shown in FIG. 4, the water trap 3 has an empty room in the interior, and includes a reservoir 31 which stores a liquid component separated from a gas obtained from a living body, on the side of the bottom plate. A suction pipe 33 is disposed in the front plate 32 of the water trap 3. In the suction pipe, a suction port 33a that is to be connected to a sampling tube from which a respiratory gas of the patient is taken out is disposed.

The suction port 33a communicates with an inner tube 34a which extends into an upper front chamber 34 in the reservoir 31 disposed inside the water trap 3. A gas is discharged from an opening of the inner tube 34a toward the reservoir 31. In the upper front chamber 34 of the reservoir 31, an opening 35a of a guiding tube 35 for guiding out the sample gas is opened in a sidewall which is in the vicinity of an uppermost portion. In the upper front chamber 34, a hydrophobic filter 34b is disposed between the opening 35a of the guiding tube 35 and the inner tube 34a. A liquid component contained in a gas which reaches from the inner tube 34a into the reservoir 31 is separated by the hydrophobic filter 34b, so that the gas from which the liquid component is separated is guided out from the guiding tube 35.

An upper rear chamber 36 having a slender lidded cylindrical shape is disposed at a position adjacent to the upper front chamber 34 of the reservoir 31. In the upper rear chamber 36, an opening 37a of a vacuum tube 37 for sucking a gas from the reservoir 31 is opened in a sidewall which is in the vicinity of an uppermost portion. A hydrophobic filter 36b is disposed between the opening 37a of the vacuum tube 37 and the reservoir 31. A liquid component contained in a gas which is sucked from the reservoir 31 into the upper rear chamber 36 is separated by the hydrophobic filter 36b, and then the gas is sucked into the opening 37a of the vacuum tube 37.

As shown in FIG. 3, an outlet opening portion 35C of the guiding tube 35 is connected to a main discharge pipe 39A which is projectingly formed on the back plate 38 of the water trap 3. An outlet opening portion 37C of the vacuum tube 37 is connected to a sub discharge pipe 39B which is projectingly formed on the back plate 38 of the water trap 3.

In the thus-configured water trap 3, a respiratory gas of the patient reaches the suction pipe 33 through the sampling tube, and then arrives in an upper portion of the reservoir 31 through the inner tube 34a. In the portion, a liquid component which is liquefied by condensation or the like is stored in the bottom side of the reservoir 31. As described above, the hydrophobic filters 34b, 36b separate liquid, and cause the liquid to be confined in the reservoir 31.

Figure 5:
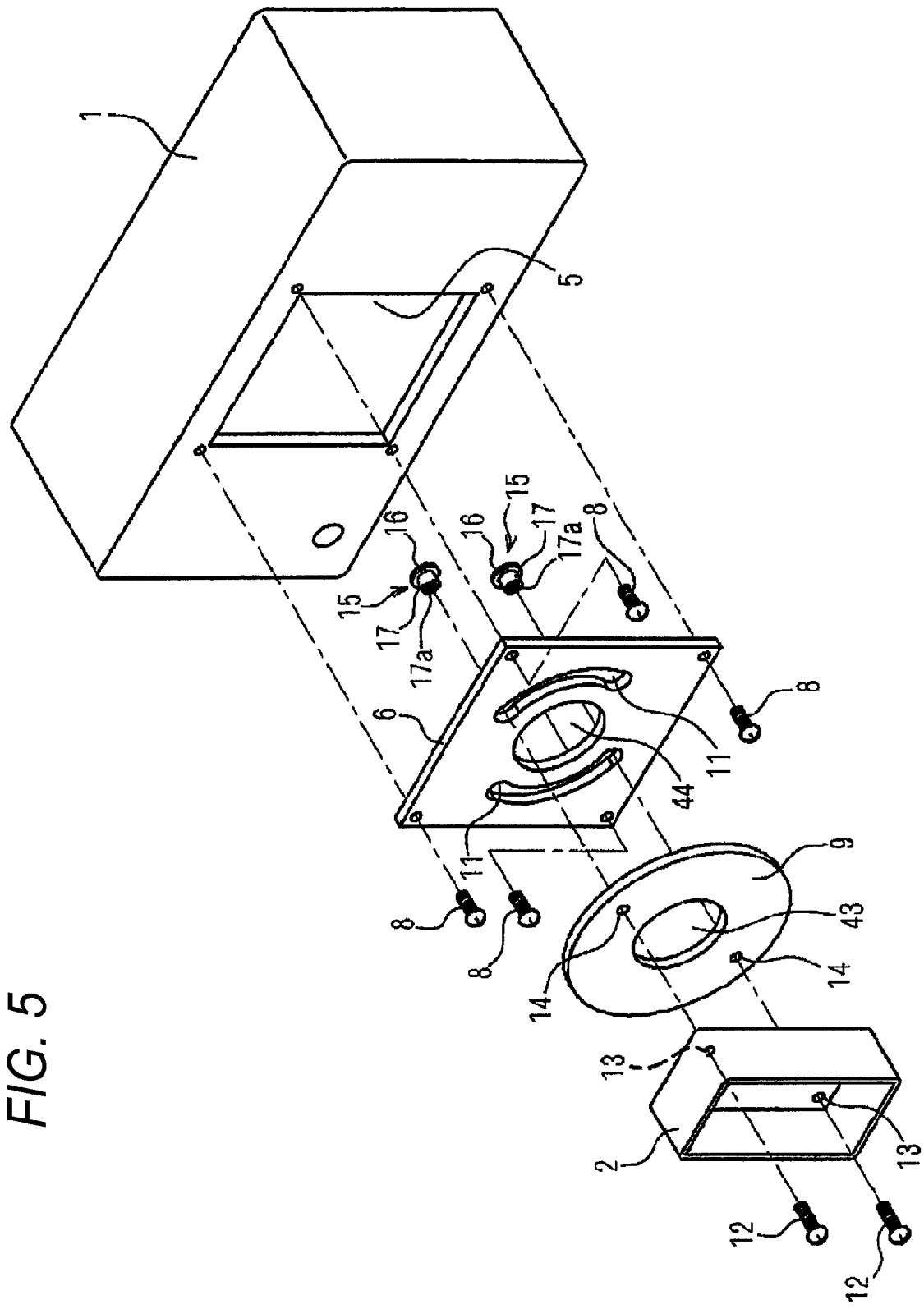
FIG. 5 is an assembly perspective view of the gas analyzer of the first embodiment of the invention.

In the case 1, as shown in FIG. 5, an opening 5 is formed in a portion where the holder portion 2 is to be positioned. The opening 5 is formed by cutting away the front plate of the case 1 in, for example, a square shape having four sides which are slightly longer than the long sides of the holder portion 2. The opening 5 is covered by a frame 6 which has, for example, a square shape that is slightly larger than the opening 5. Screws 8 are inserted through holes in the four edges of the frame 6, and then screwed into threaded screw holes formed in an edge portion adjacent to the opening 5 of the case 1, respectively, whereby the frame 6 is fixed to the case 1.

In the frame 6, double threaded groove holes 11, 11 are formed in an arcuate shape which constitutes a part of the circumference of a circle. The lengths of the groove holes 11, 11 are extended in accordance with the rotation angle of the holder portion 2. In the embodiment, the groove holes have a length which enables the holder portion 2 to be rotated by 90 degrees.

A disk-like plate 9 is interposed between the frame 6 and the holder portion 2. In the bottom plate of the holder portion 2, holes through which screws 12 are inserted are formed in a pair of edges which are connected to each other by a diagonal of the rectangle conforming to the shape of the bottom plate, respectively. Holes 14 corresponding to the holes 13 of the holder portion 2 are formed in an area of the plate 9 on which the holder portion 2 is to be placed. The screw portions of the screws 12 are passed through the holes 13 of the holder portion 2 and the holes 14 of the plate 9 to reach the groove holes 11 of the frame 6.

Studs 15 are disposed to extend in the direction of the face of the frame 6 opposed to the screws 12 toward the groove holes 11. In each of the studs 15, a head portion 16 has a disk-like shape, the diameter of the head portion is larger than the widths of the groove holes 11, a leg portion 17 is projected from the middle part of the rear face of the disk-like head portion 16, and the diameter of the leg portion 17 is slightly smaller than the widths of the groove holes 11. Therefore, the studs 15 can slide along the groove holes 11 in a state where the leg portions 17 are inserted through the groove holes 11, respectively.

In each of the studs 15, moreover, a threaded groove 17a which is to be screwed with the corresponding one of the screws 12 is formed so as to be directed from the end face toward the head portion 16. When the screws 12 are inserted so as to pass through the holes 13 of the holder portion 2 and the holes 14 of the plate 9, the studs 15 are inserted toward the groove holes 11 in the direction of the face of the frame 6 opposed to the screws 12, and the screws 12 are screwed with the threaded grooves 17a formed in the leg portions 17 of the studs, respectively, the holder portion 2 is fixed to the plate 9, and the head portions 16 of the studs 15 butt against one face of the frame 6 in a state where the leg portions 17 of the studs 15 are fitted into the groove holes 11. In this way, a rotation mechanism is configured by the frame 6 having the groove holes 11 functioning as a sliding groove, and the studs 15 functioning as sliding members which are fixed to the holder portion 2.

Figure 6:
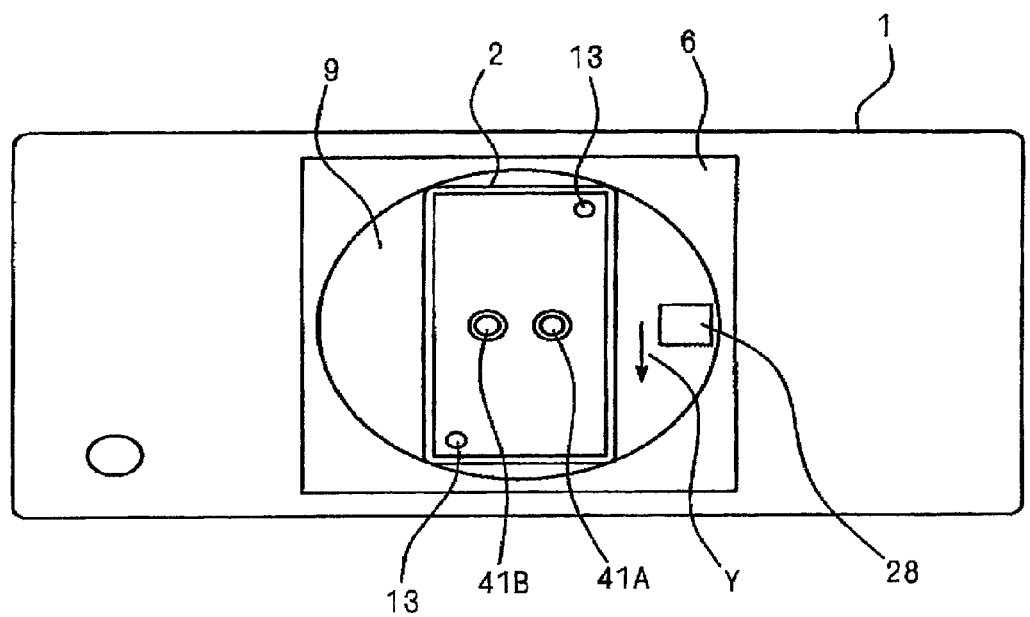
FIG. 6 is a front view showing a state where the water trap is applied to the gas analyzer of the first embodiment of the invention.
Figure 7:
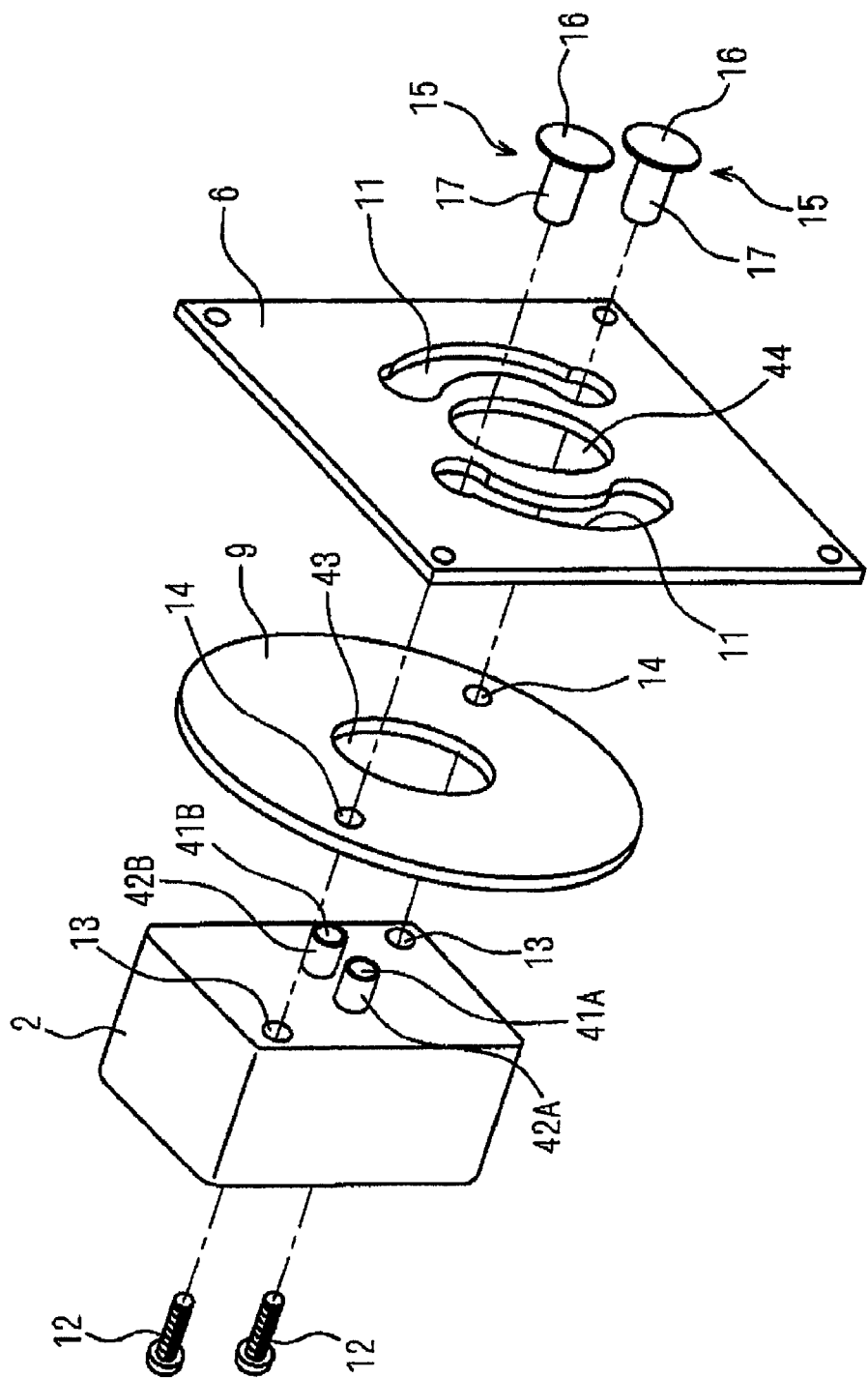
FIG. 7 is an assembly perspective view of a portion of the gas analyzer of the first embodiment of the invention.

In the back plate of the holder portion 2, as shown in FIGS. 6 and 7, a main insertion hole 41A into which the main discharge pipe 39A of the water trap 3 is to be inserted and fitted, and a sub insertion hole 41B into which the sub discharge pipe 39B of the water trap 3 is to be inserted and fitted are formed. The main insertion hole 41A and the sub insertion hole 41B communicate with the interiors of a main projected pipe 42A and sub projected pipe 42B which are projected from the holder portion 2 toward the plate 9, respectively. In the plate 9 and the frame 6, circular through holes 43, 44 are respectively formed in the range where the main projected pipe 42A and the sub projected pipe 42B are rotated due to rotation of the holder portion 2.

Figure 8:
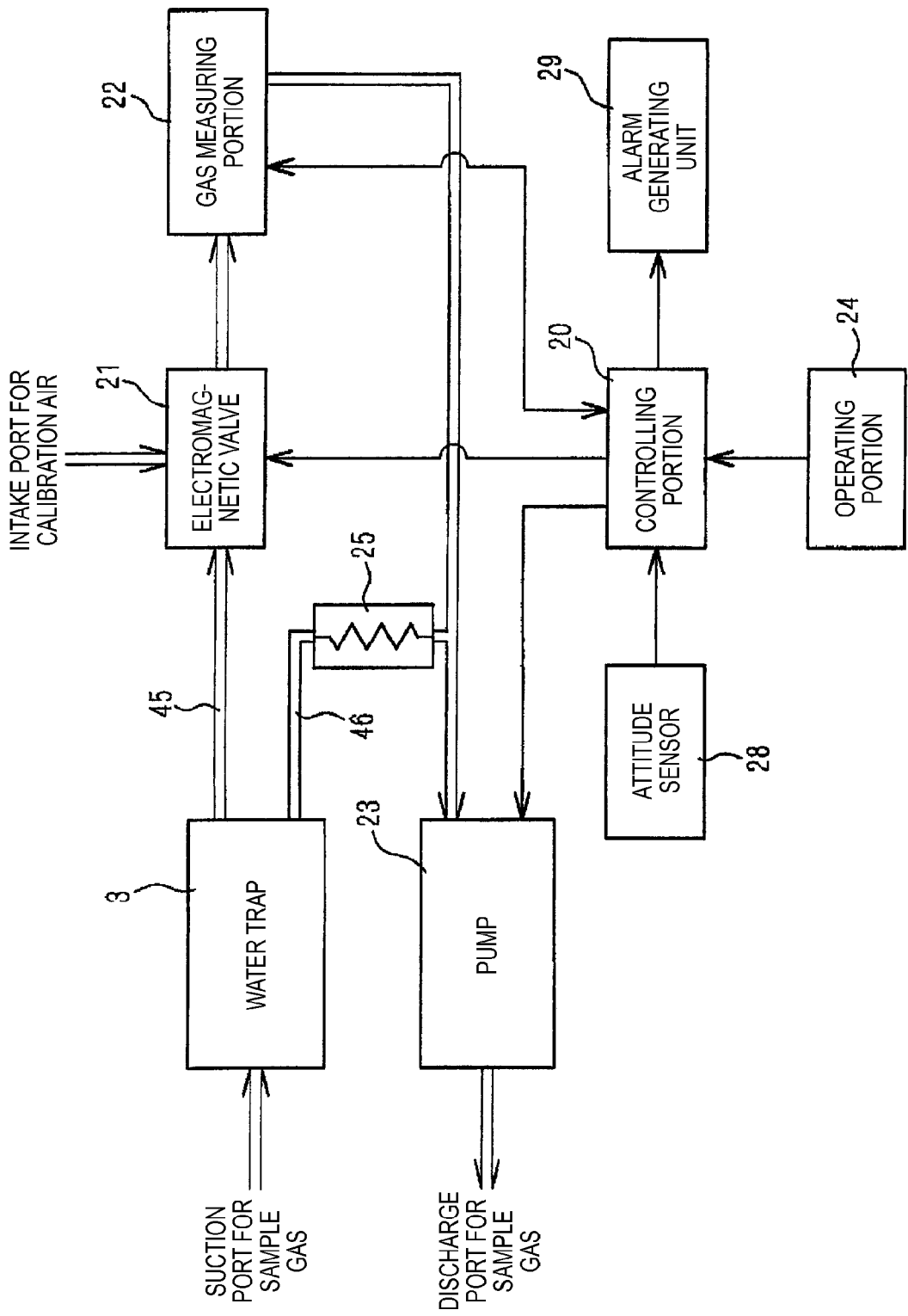
FIG. 8 is a block diagram showing the internal configuration of the gas analyzer of the first embodiment of the invention.

An intake tube 45 and a suction tube 46 which are in the case 1, and which are shown in FIG. 8 are connected to the main projected pipe 42A and sub projected pipe 42B which are projected from the holder portion 2, respectively. The intake tube 45 and the suction tube 46 are moved in accordance with the rotation of the holder portion 2. Since the tubes are disposed while passing through the circular through holes 43, 44, respectively, the rotation is not interrupted.

As shown in FIG. 8, the gas analyzer includes, in the case 1, an electromagnetic valve 21, a gas measuring portion 22, a pump 23, and a controlling portion 20. An operating portion 24 in which switches and the like are disposed is placed on a wall portion of the case 1, so that a command or the like can be transmitted to the controlling portion 20. The portions indicated by the double lines are tubes through which a gas flows.

A gas which is taken in through the intake tube 45 is sent to the gas measuring portion 22 through the electromagnetic valve 21. The gas measuring portion 22 measures the concentration, respiratory volume, and the like of carbon dioxide, oxygen, nitrogen monoxide, a volatile anesthetic, etc., by means of related-art techniques. Information related to results of measurements is sent from the controlling portion 20 to a monitor device or the like which is not shown, to be displayed thereon. Alternatively, the information may be displayed on the gas analyzer.

A gas which is taken in through the suction tube 46, and that which is discharged from the gas measuring portion 22 are sucked by the pump 23 to be discharged. An appropriate resistor 25 is interposed between the suction tube 46 and the pump 23, thereby controlling the gas flow.

An attitude sensor 28 is applied to the plate 9, and the output of the attitude sensor 28 is sent to the controlling portion 20. An alarm generating unit 29 which is configured by a speaker and a driver is connected to the controlling portion 20. The attitude sensor 28 detects the attitude of the holder portion 2 with respect to the direction of gravitational force, and is referred to as a three-axis acceleration sensor or the like. The attitude sensor transmits a detection signal in the case where the holder portion 2 is not in a predetermined attitude in which the reservoir 31 is positioned in the lowermost portion in the direction of gravitational force in the held water trap 3. When the controlling portion 20 receives the detection signal from the attitude sensor 28, the controlling portion drives the alarm generating unit 29 to generate an alarm sound. Alternatively, the alarm generating unit 29 may generate light or output a character display in place of the sound generation. In the case where the holder portion is not in the predetermined attitude in which the reservoir 31 is positioned in the lowermost portion in the direction of gravitational force in the water trap 3, the alarm generating unit 29 may send the detection signal to the monitor device which is not shown, and the monitor device may generate the alarm sound.

In the thus-configured gas analyzer, a state where, as shown in FIG. 1, the case 1 is disposed in a low profile state, the holder portion 2 is in a vertically elongated state, and the reservoir 31 of the water trap 3 exists in the lower side in the holder portion 2 is the usual state. The state where the arrow Y is downward directed is the adequate state. In this state, as described above, a liquid component contained in a gas which reaches into the reservoir 31 is separated, and then stored in the reservoir 31, and hence the analyzer can properly operate.

In the state of FIG. 1, the installation area of the gas analyzer is wide. Therefore, a situation where the place in which the analyzer is to be disposed cannot be ensured may possibly occur. In such a case, the analyzer can be disposed in a state where, as shown FIG. 9, the analyzer is in a vertically elongated state. When the case 1 in the state of FIG. 1 is simply rotated by 90 degrees and disposed on a desk or the like to attain the state of FIG. 9, the attitude sensor 28 transmits the detection signal, and an alarm is announced by the alarm generating unit 29.

Figure 9:
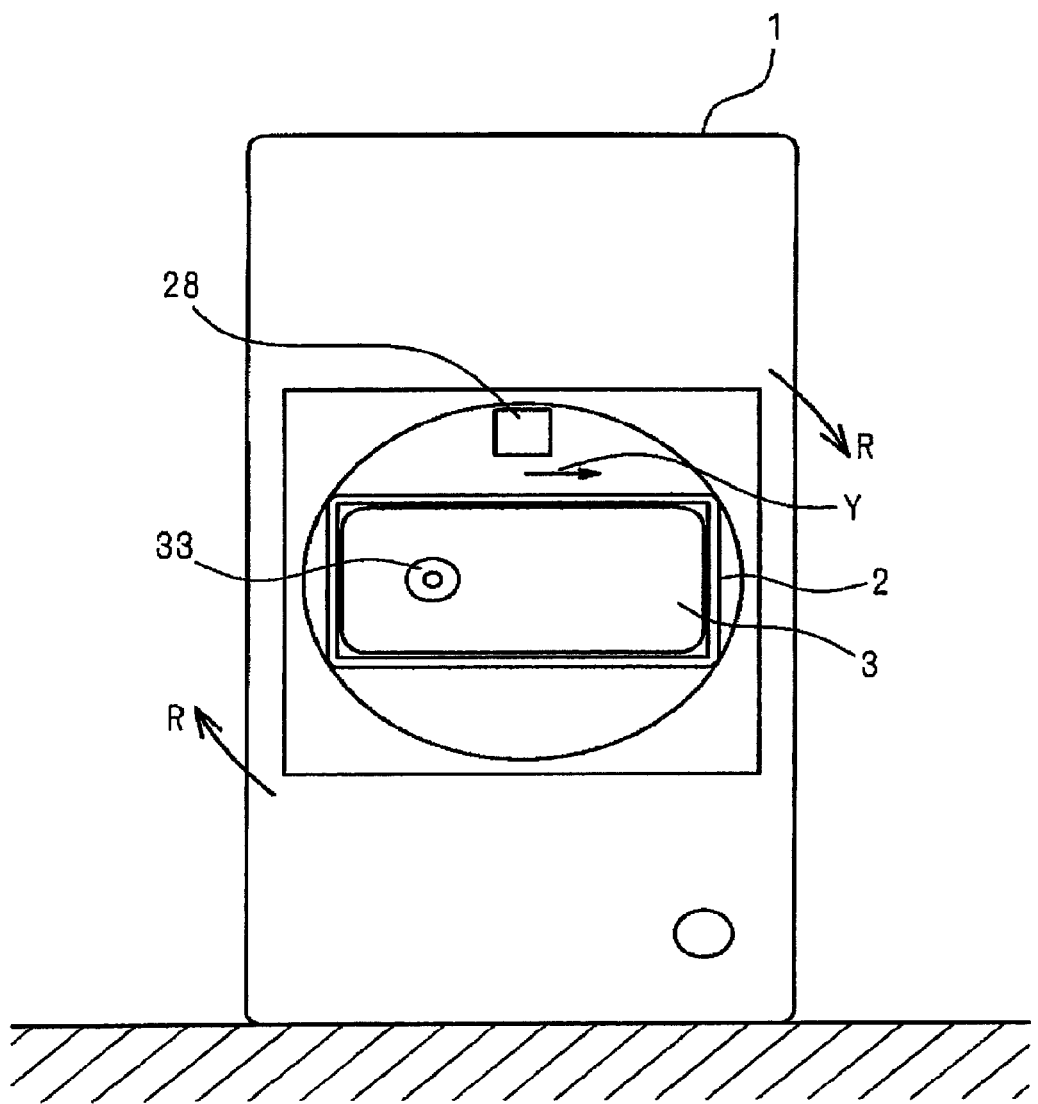
FIG. 9 is a front view showing a condition where the gas analyzer of the first embodiment of the invention is disposed in a longitudinally elongated state.
Figure 10:
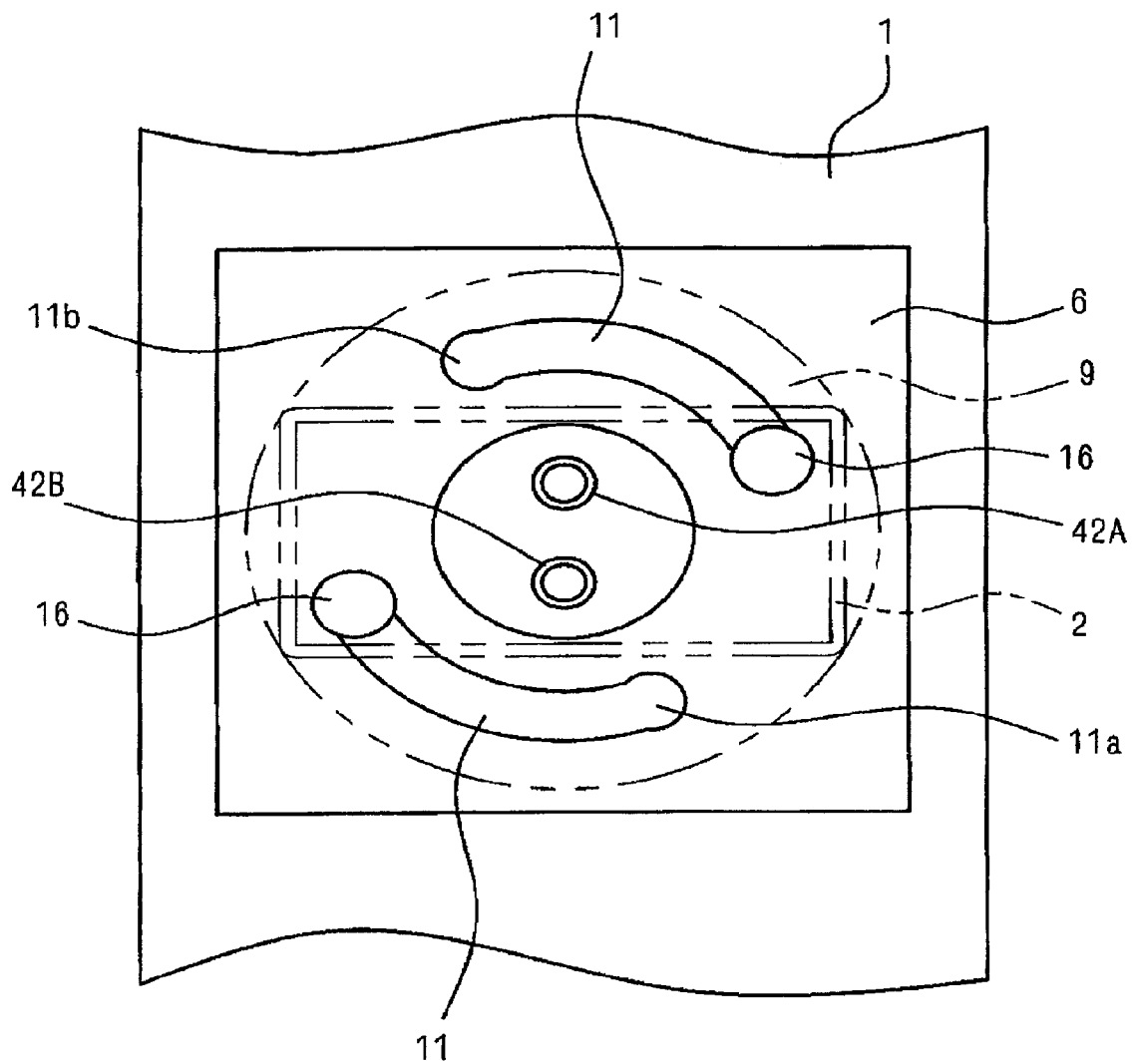
FIG. 10 is a view showing a portion such as a holder portion in the back direction, in the case where the gas analyzer of the first embodiment of the invention is set in the state of FIG. 9.
Figure 11:
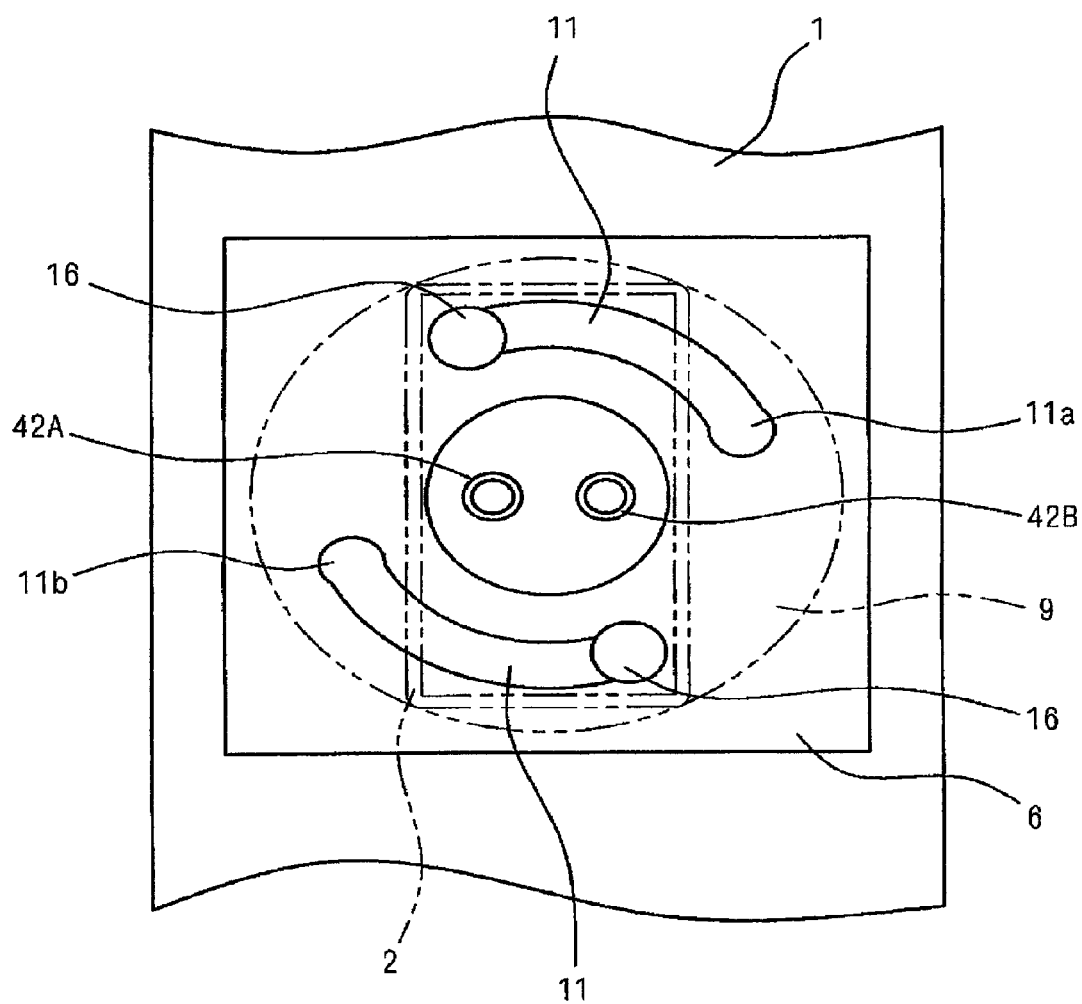
FIG. 11 is a view showing a portion in a state where the holder portion in the state of FIG. 9 is right-rotated by 90 degrees.
Figure 12:
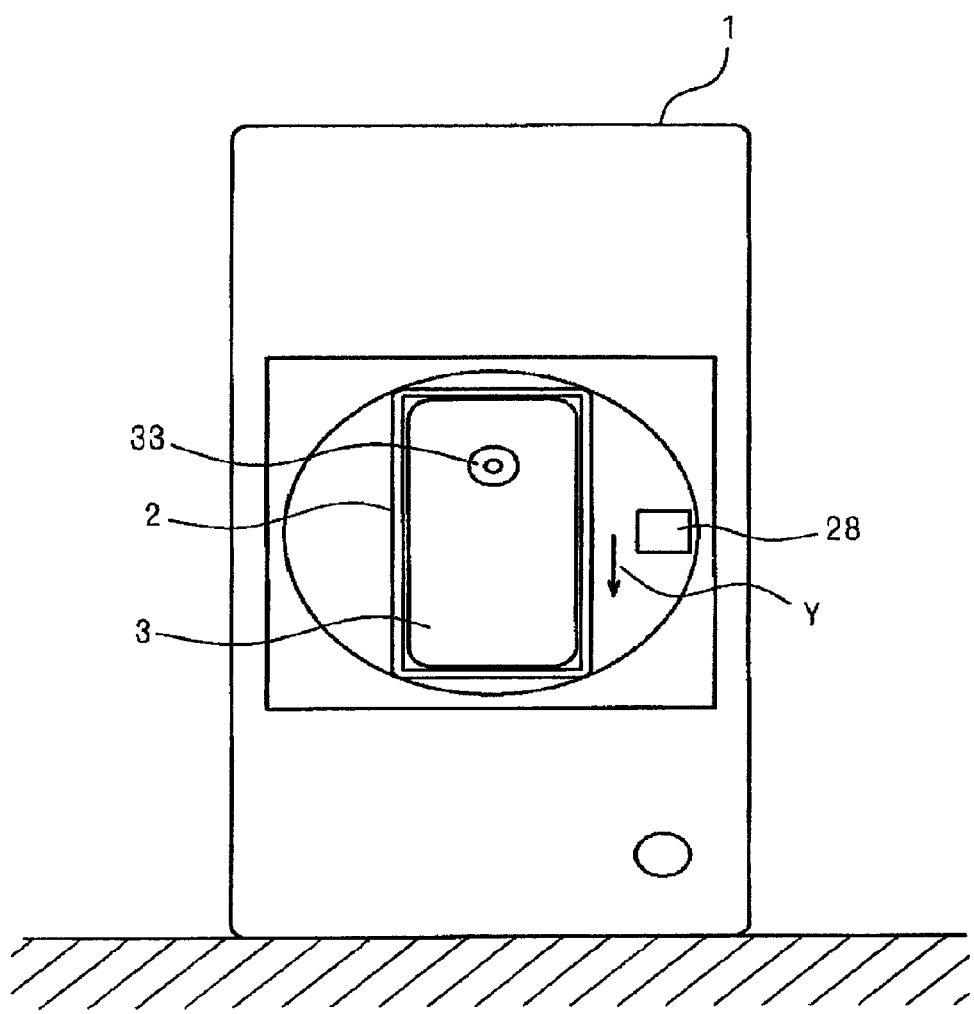
FIG. 12 is a front view of the gas analyzer of the first embodiment of the invention in the state of FIG. 11.

In the state of FIG. 9, therefore, the holder portion 2 is right-rotated by 90 degrees as indicated by the arrow R. As shown in FIGS. 10 and 11 as viewed from the side of the head portions 16 of the studs 15, then, the leg portions 17 of the studs 15 slide from one end portions of the groove holes 11 along the groove holes 11 in the state where the leg portions 17 are inserted through the groove holes 11, and reach the other end portions of the groove holes 11. As shown in relationship with the case 1, the holder portion is rotated by 90 degrees from the state of FIG. 9 to obtain a state where, as shown in FIG. 12, the holder portion 2 and the case 1 are elongated in the vertical direction of the figure, and the reservoir 31 of the water trap 3 exists in the lower side of the holder portion 2. At this time, the adequate state where the arrow Y is downward directed is attained. In this state, similarly with the state of FIG. 1, a liquid component contained in a gas which reaches into the reservoir 31 is separated, and then stored in the reservoir 31. Therefore, the analyzer can properly operate.

As shown in FIGS. 10 and 11, the both end portions of the groove holes 11 are formed into circular portions 11a, 11b having a diameter which is very slightly longer than the widths of the intermediate portions of the groove holes 11. In the intermediate portions of the groove holes 11, therefore, the leg portions 17 of the studs 15 butt against edge portions of the groove holes 11. In the circular portions 11a, 11b formed in the both end portions of the groove holes 11, by contrast, the leg portions 17 of the studs 15 do not butt against the edge portions of the groove holes 11, and remain in the middle parts of the circular portions 11a, 11b. In other words, the analyzer includes a locking unit which locks the holding portion 2 in the case where the holder portion 2 is rotated by a predetermined angle or 90 degrees.

In the above, the configuration using the rotation mechanism which can be rotated by 90 degrees has been exemplarily described. Alternatively, the distances from the rotation center to the two groove holes 11 may be made different from each other, the positions of the end portions of the groove holes may be made slightly different from each other, and the studs 15 may be made correspondent with the groove holes, thereby enabling rotation of 360 degrees. It is a matter of course that a configuration for rotation of 270 degrees or that for 180 degrees is enabled. In this case, as described above, a configuration corresponding to the circular portions 11a, 11b having a diameter which is very slightly larger than the widths of the intermediate portions of the groove holes 11 is disposed at each rotation of 90 degrees, so that the holder portion can be locked at each rotation of 90 degrees.

Figure 13:
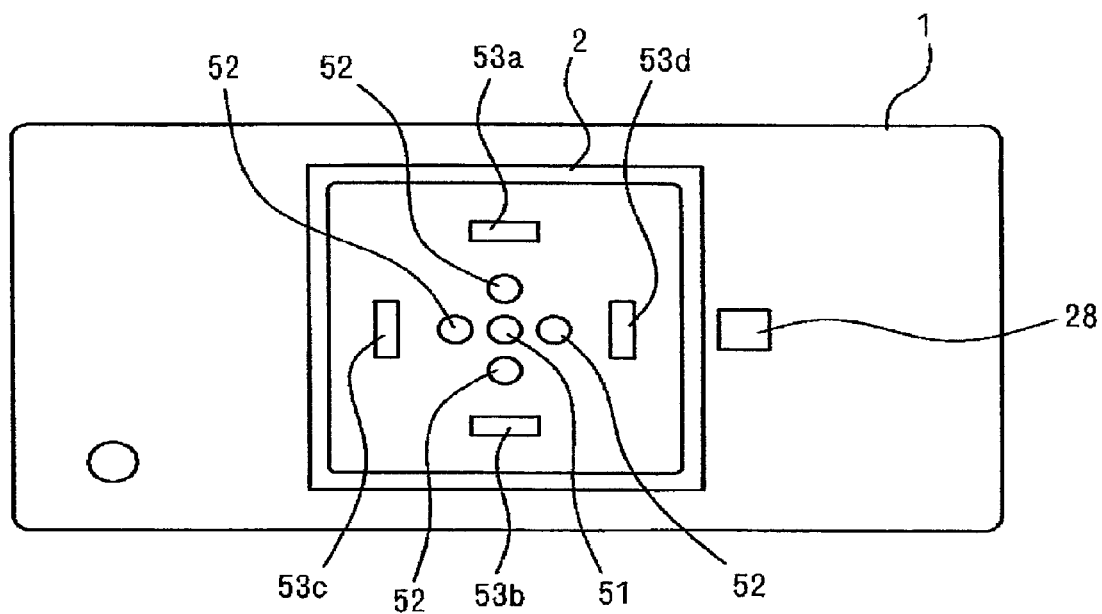
FIG. 13 is a front view of a gas analyzer of a second embodiment of the invention.

Next, a gas analyzer of a second embodiment will be described. In the gas analyzer, as shown in FIG. 13, a main flow path hole 51 is formed in the middle of the back plate of the holder portion 2, and four sub flow path holes 52 are formed so as to surround the main flow path hole 51. The four sub flow path holes 52 are formed respectively at positions which are sequentially rotated in steps of 90 degrees while being centered at the main flow path hole 51.

Figure 16:
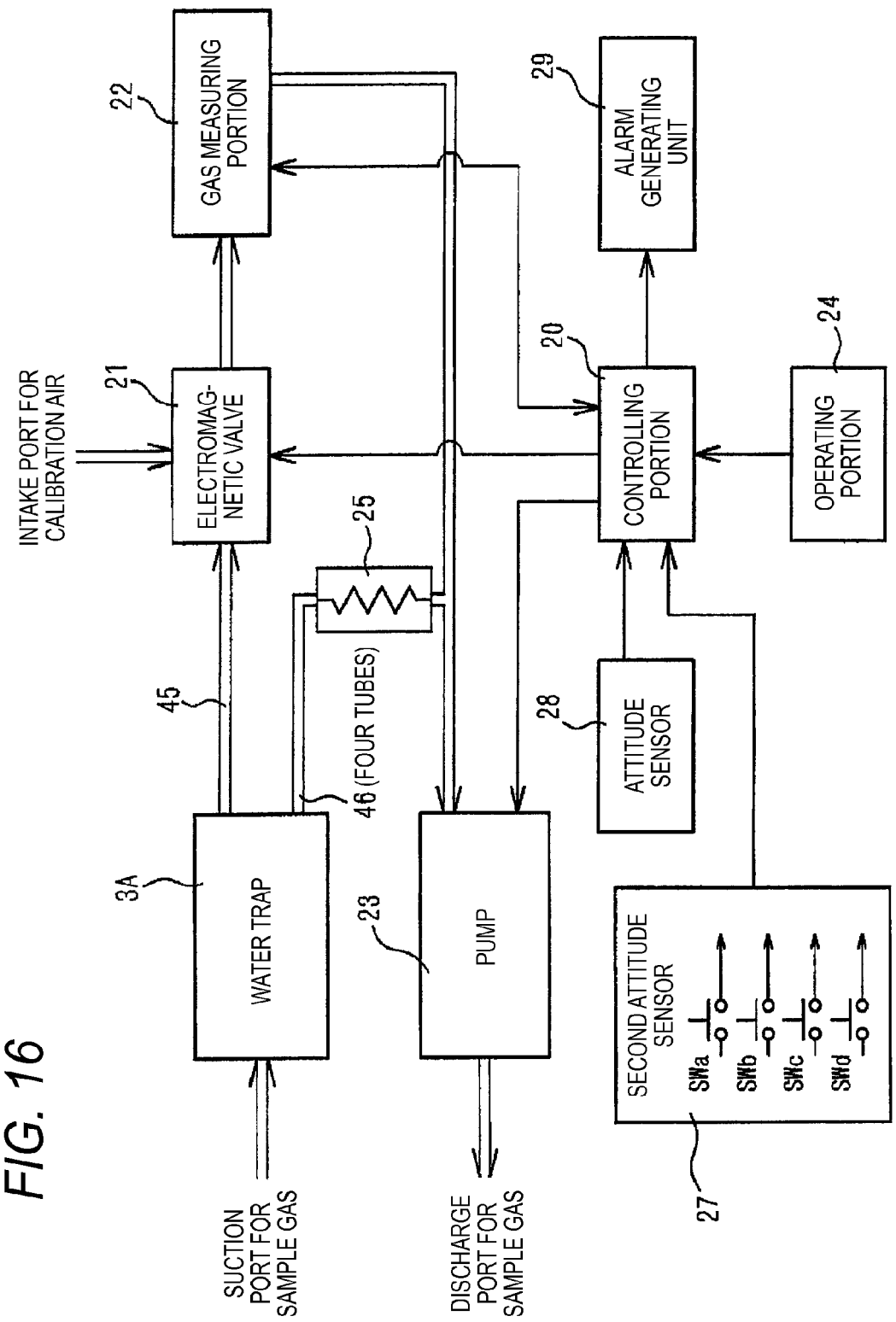
FIG. 16 is a block diagram showing the internal configuration of the gas analyzer of the second embodiment of the invention.
Figure 17A:
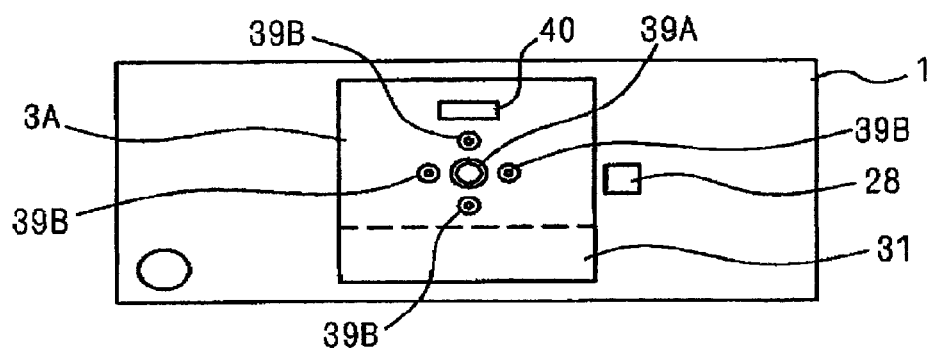
FIGS. 17A to 17D are views showing a state where the state of disposing the gas analyzer of the second embodiment of the invention is changed, while viewing through the back face of the water trap.
Figure 17B:
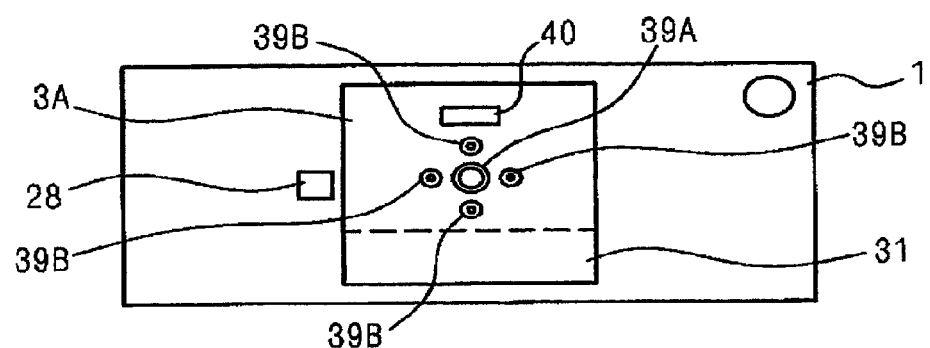
Figure 17C:
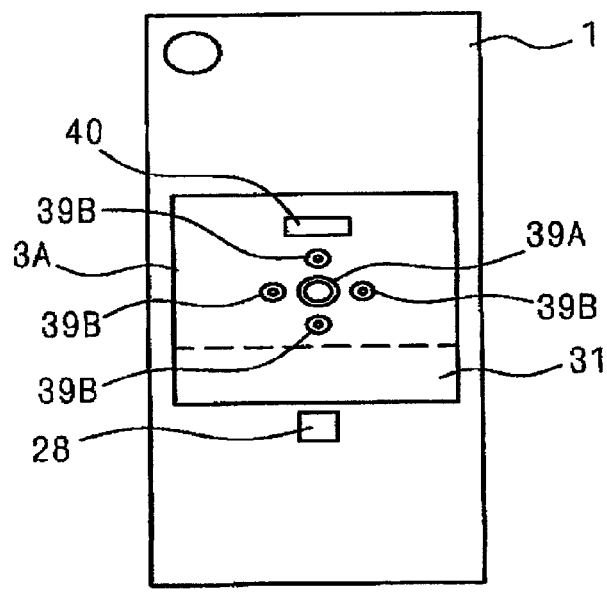
Figure 17D:
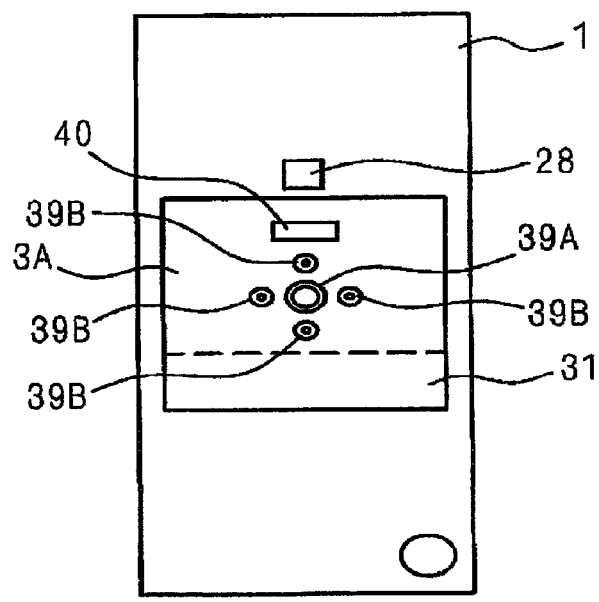

Four rectangular holes 53a to 53d are formed in the directions of line segments connecting the four sub flow path holes 52 while being centered at the main flow path hole 51. On the side of the rear face of the back plate of the holder portion 2, a main projection pipe 41A which corresponds to the main flow path hole 51 and the sub flow path holes 52, and which is as shown in FIG. 7, and four sub projection pipes 41B which correspond to the sub flow path holes 52, and which are as shown in FIG. 7 are projectingly formed. The main projection pipe 41A is connected to a intake tube 45 shown in FIG. 16 which shows the internal configuration of the gas analyzer of the second embodiment, and suction tubes 46 are connected to the four sub projection pipes 41B, respectively, so that, as a whole, four tubes extend to the pump 23 as shown in FIG. 16. In this way, the embodiment includes the main flow path through which the gas is flown from a water trap 3A that is the liquid separator to the gas measuring portion 21, and the sub flow paths for applying a sucking operation on the reservoir 31.

Figure 14:
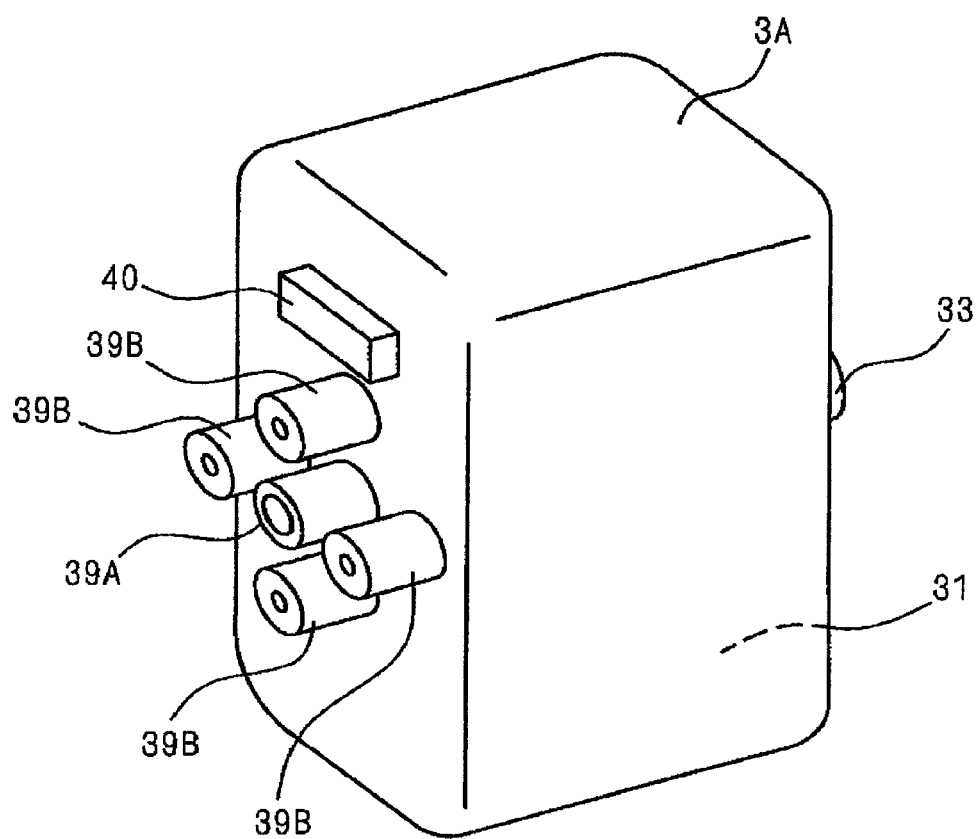
FIG. 14 is a perspective view showing a water trap which is applied to the gas analyzer of the second embodiment of the invention.

FIG. 14 is an external view of the water trap 3A. The suction pipe 33 is disposed in the front plate 32 of the water trap 3A. In the suction pipe, the suction port 33a that is to be connected to a sampling tube from which a respiratory gas of the patient is taken out is disposed. The internal configuration including the portion which is connected to the suction port 33a of the water trap 3A is basically identical with that of the water trap 3 shown in FIG. 4.

Figure 15:
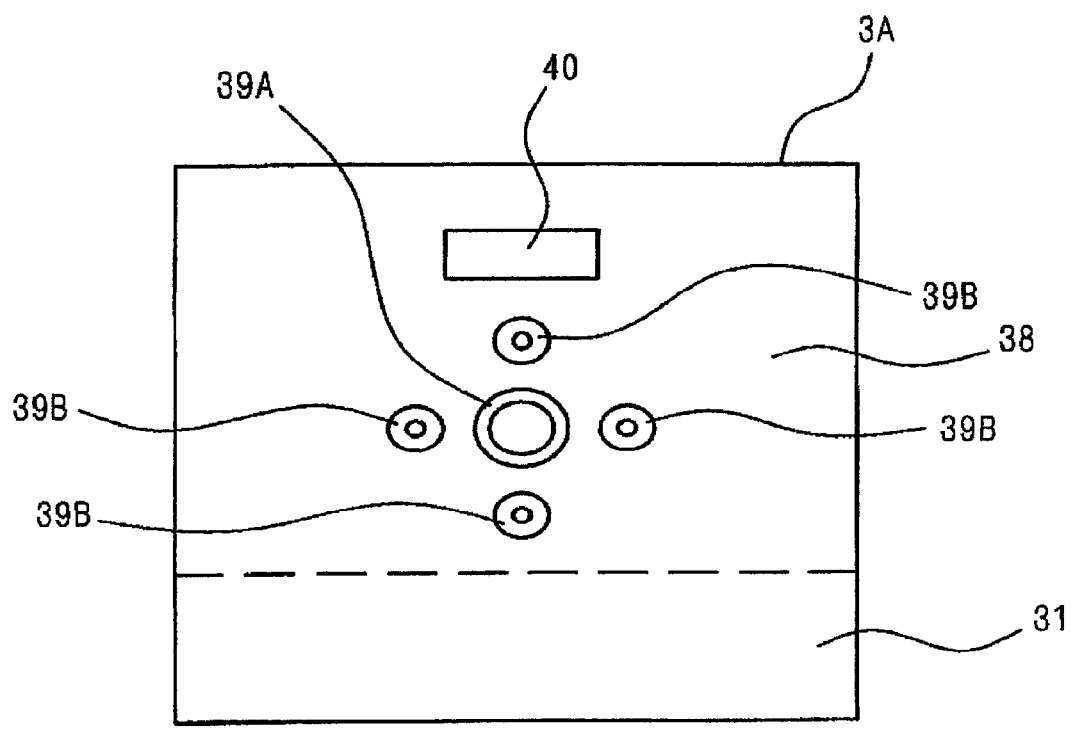
FIG. 15 is a rear view showing the water trap which is applied to the gas analyzer of the second embodiment of the invention.

As shown in FIG. 15, the main discharge pipe 39A is projectingly formed on the back plate 38 of the water trap 3A. Four sub discharge pipes 39B are formed respectively at positions which are sequentially rotated in steps of 90 degrees while being centered at the main discharge pipe 39A. The internal configuration of the water trap 3A which is connected with the main discharge pipe 39A is identical with that shown in FIG. 4. With respect to the sub discharge pipes 39B, however, four routes each formed by the internal configuration of the sub discharge pipe 39B shown FIG. 4 are disposed.

FIG. 14 shows the state where the reservoir 31 is positioned in the lowermost portion in the direction of gravitational force in the water trap 3A. In this state, a projection piece 40 which laterally elongates is formed above the uppermost one of the four sub discharge pipes 39B which are projectingly formed on the back plate 38.

The projection piece 40 has a configuration in which it is fitted into any one of the rectangular holes 53a to 53d of the holder portion 2. The main discharge pipe 39A is fitted into the main flow path hole 51, and the four sub discharge pipes 39B are fitted into the sub flow path holes 52. When the case 1 is in the state of FIG. 13, therefore, the water trap 3A which is in the state of FIG. 15 can be inserted into the holder portion 2 to be fitted and held thereto. Moreover, the water trap 3A which is rotated rightward or leftward by 90 degrees from the state of FIG. 15 can be inserted into the holder portion 2 in the state of FIG. 13 to be fitted and held thereto. Furthermore, the water trap 3A which is vertically inverted from the state of FIG. 15 can be inserted into the holder portion 2 in the state of FIG. 13 to be fitted and held thereto.

Contacts SWa to SWd which are pressed by insertion of the projection piece 40 to be closed are disposed on the bottom faces of the rectangular holes 53a to 53d of the holder portion 2, respectively. As shown in FIG. 16, the contacts SWa to SWd function as a second attitude sensor 27. On/off information of the contacts SWa to SWd of the second attitude sensor 27 is fetched into the controlling portion 20.

The second attitude sensor 27 detects the attitude of the case 1 with respect to the direction of gravitational force, or detects in which one of the four states of FIGS. 17A to 17D the case 1 is, and sends a signal to the controlling portion 20. As apparently shown by a circle drawn on the front panel of the case 1, the case 1 has four attitude modes.

The case attitudes are indicated respectively by a to d in accordance with FIGS. 17A to 17D. When the projection piece 40 is fitted to each of the rectangular holes 53a to 53d, the state where the reservoir 31 is positioned in the lowermost portion in the direction of gravitational force in the water trap 3A is attained. Namely, combination of the contacts SWa to SWd which are closed, and the attitudes a to d of the case 1 are as shown in FIG. 18. In the case of a combination other than these combinations, it is detected that the attitude of the water trap 3A which is the liquid separator is not in the predetermined attitude in which the reservoir 31 is positioned in the lowermost portion in the direction of gravitational force in the water trap 3A, and the alarm generating unit 29 generates an alarm. Alternatively, a detected signal may be sent to the monitor device which is not shown, and the monitor device may generate an alarm.

In the thus-configured gas analyzer of the embodiment, when the attitude of the case 1 is any one of FIGS. 17A to 17D, the water trap 3A can be inserted and fitted into the holder portion 2 while the water trap 3A is set to the attitude (adequate attitude) in which the reservoir 31 is positioned in the lowermost portion in the direction of gravitational force in the water trap 3A, and the gas analyzer can be used in the adequate state.

In the case where the attitude of the case 1 is any one of FIGS. 17A to 17D, when the water trap 3A is not inserted and fitted into the holder portion while the water trap is set to the adequate attitude, moreover, an alarm is generated by the attitude sensor 28, the second attitude sensor 27, the alarm generating unit 29, and the controlling portion 20, and it is informed that the water trap is inadequately installed or attached.

The embodiment is configured so as to correspond to a case where the case 1 is rotated by any one of 90 degrees, 180 degrees, and 270 degrees. Alternatively, the gas analyzer may be configured in the following manner. The configurations of the main flow path hole 51 and the sub flow path holes 52 are changed, and the water trap 3A is differently configured in accordance with the change, so that, when the water trap is rotated only by 90 degrees, or by 90 degrees and 270 degrees, the water trap 3A can be inserted and fitted into the holder portion 2 while the water trap 3A is set to the attitude (adequate attitude) in which the reservoir 31 in the water trap 3A is positioned in the lowermost portion in the direction of gravitational force. Also in the alternative, the gas analyzer can adequately operate.

According to an aspect of the invention, the analyzer includes the reservoir which stores the liquid component separated from the gas, and the holder portion which holds the liquid separator is mounted on the rotation mechanism. Therefore, the analyzer can operate in a state where the liquid separator functions properly.

According to an aspect of the invention, the analyzer includes the locking unit which locks the holding portion in the case where the holder portion is rotated to the position where the reservoir is in the lowermost portion in the direction of gravitational force in the held liquid separator. Therefore, the holder can be locked in the state where the liquid separator functions properly, and the adequate operation of the analyzer can be ensured.

According to an aspect of the invention, the analyzer includes the sensor which detects the attitude of the holder portion with respect to the direction of gravitational force. Therefore, it is possible to detect the attitude of the holder portion.

According to an aspect of the invention, the analyzer is configured so that, in the case where the holder portion detected by the sensor does not have a predetermined attitude in which the reservoir is positioned in the lowermost portion in the direction of gravitational force in the held liquid separator, an alarm is generated. When the holder portion is not in the state where the liquid separator functions properly, therefore, an alarm is generated, and it is possible to know an inadequate state.

According to an aspect of the invention, the analyzer includes the transmitting unit which, in the case where the attitude of the holder portion detected by the sensor is not in the predetermined one in which the reservoir is positioned in the lowermost portion in the direction of gravitational force in the held liquid separator, transmits the detection signal. Depending on the attitude of the holder portion, therefore, an appropriate device can receive the detection signal, and an alarm or the like can be output.

According to an aspect of the invention, the analyzer includes the holding unit in the holder portion that includes the reservoir for storing the liquid component separated from the gas, and that holds the liquid separator which guides the gas from which the liquid component is separated, to the gas measuring portion, and the holding unit holds the liquid separator in one of attitudes which are different from one another in steps of 90 degrees. Therefore, the analyzer can be caused to operate in the state where the liquid separator functions properly.

According to an aspect of the invention, the holding unit includes the main flow path through which the gas is flown from the liquid separator to the gas measuring portion, and the sub flow paths for applying a sucking operation on the reservoir. Therefore, the gas can be adequately guided from the liquid separator toward the gas measuring portion.

According to an aspect of the invention, in the face of the holder portion which is opposed to the liquid separator, the flow path port of the main flow path, and the sub flow path ports of the sub flow paths, the sub flow path ports being symmetrically placed about the flow path port of the main flow path, are formed. Therefore, the analyzer can be caused to operate in the state where the liquid separator functions properly.

According to an aspect of the invention, the analyzer includes the sensor which detects the attitude of the liquid separator held by the holder portion with respect to the direction of gravitational force. Therefore, it is possible to detect the attitude of the liquid separator.

According to an aspect of the invention, in the case where the attitude of the liquid separator is not in a predetermined one in which the reservoir is positioned in the lowermost portion in the direction of gravitational force in the liquid separator, an alarm is generated. When the analyzer is not in the state where the liquid separator functions properly, therefore, an alarm is generated, and it is possible to know an inadequate state.

According to an aspect of the invention, the analyzer includes the transmitting unit which, in the case where the attitude of the liquid separator detected by the sensor is not in the predetermined one in which the reservoir is positioned in the lowermost portion in the direction of gravitational force in the liquid separator, transmits the detection signal. Depending on the attitude of the liquid separator, therefore, an appropriate device can receive the detection signal, and an alarm or the like can be output.

We claim:

1. A gas analyzer comprising:
   a gas measuring portion which performs a measurement on a gas;
   a case which houses the gas measuring portion;
   a liquid separator which includes a reservoir for storing a liquid component separated from the gas, and which guides the gas from which the liquid component is separated, to the gas measuring portion; and
   a holder portion connectable to the case and the liquid separator, the liquid separator being configured for manual connection to the holder portion in one of a plurality of attitudes, which are different from one another in steps of 90 degrees, the holder portion being configured to enable a determination by a sensor as to whether the liquid separator is connected to the holder portion in an attitude such that the reservoir is positioned in a lowermost portion in a direction of a gravitational force in the liquid separator.

2. The gas analyzer according to claim 1, wherein the holder portion includes a main flow path through which the gas is flown from the liquid separator to the gas measuring portion, and sub flow paths for applying a sucking operation on the reservoir.

3. The gas analyzer according to claim 2, wherein, in a face of the holder portion which is opposed to the liquid separator, a flow path port of the main flow path, and sub flow path ports of the sub flow paths are formed, the sub flow path ports being symmetrically placed about the flow path port of the main flow path.

4. The gas analyzer according to claim 1, wherein the sensor detects an attitude of the liquid separator with respect to the direction of the gravitational force.

5. The gas analyzer according to claim 4, further comprising:
   an alarm unit which generates an alarm in a case where the attitude of the liquid separator detected by the sensor is not in a predetermined attitude in which the reservoir is positioned in the lowermost portion in the direction of the gravitational force in the liquid separator.

6. The gas analyzer according to claim 4, further comprising:
a transmitting unit which transmits a detection signal in a case where the attitude of the liquid separator which is detected by the sensor is not in a predetermined attitude in which the reservoir is positioned in the lowermost portion in the direction of the gravitational force in the liquid separator.

7. The gas analyzer according to claim 1, wherein the holder portion includes a rotation mechanism configured such that movement of the holder portion causes a gravitational force to rotate the holder portion along an axis so that the reservoir is positioned in a lowermost portion in the direction of the gravitational force in the liquid separator.

8. A gas analyzer comprising:
a gas measuring portion which performs a measurement on a gas;
a case which houses the gas measuring portion;
a liquid separator which includes a reservoir for storing a liquid component separated from the gas;
a suction pipe which is disposed on the liquid separator, and which includes a suction port that is configured to be connected to a sampling tube that receives respiratory air to be analyzed;
a holder portion which holds the liquid separator; and
a rotation mechanism which mounts the holder portion to the case, wherein the holder portion is rotatable with respect to the case so that the reservoir is positioned in a lowermost portion in a direction of a gravitational force in the liquid separator.

9. The gas analyzer according to claim 8, wherein the rotation mechanism is configured such that movement of the holder portion causes a gravitational force to rotate the holder portion along an axis so that the reservoir is positioned in a lowermost portion in the direction of the gravitational force in the liquid separator.

10. A gas analyzer comprising:
a gas measuring portion which performs a measurement on a gas;
a case which houses the gas measuring portion;
a holder portion that holds a liquid separator which includes a reservoir for storing a liquid component separated from the gas, and which guides the gas from which the liquid component is separated, to the gas measuring portion;
a suction pipe which is disposed on the liquid separator, and which includes a suction port that is configured to be connected to a sampling tube that receives respiratory air to be analyzed; and
a holding unit which is configured to hold the liquid separator in one of a plurality of attitudes which are different from one another in steps of 90 degrees, wherein the liquid separator is movable with respect to the holder portion so that the reservoir is positioned in a lowermost portion in a direction of a gravitational force in the liquid separator.

11. The gas analyzer according to claim 10, wherein the holder portion includes a rotation mechanism configured such that movement of the holder portion causes a gravitational force to rotate the holder portion along an axis so that the reservoir is positioned in a lowermost portion in the direction of the gravitational force in the liquid separator.

* * * * *